United States Patent
Topchiashvili et al.

(10) Patent No.: US 9,737,698 B2
(45) Date of Patent: Aug. 22, 2017

(54) METHOD AND SYSTEM FOR TREATING PATIENTS WITH ALZHEIMER DISEASE

(71) Applicants: Mikhail Topchiashvili, Brooklyn, NY (US); Luba Chigirinskay, Brooklyn, NY (US); Marika Cherfas, Brooklyn, NY (US)

(72) Inventors: Mikhail Topchiashvili, Brooklyn, NY (US); Luba Chigirinskay, Brooklyn, NY (US); Marika Cherfas, Brooklyn, NY (US)

(73) Assignees: Givi Topchiashvili, Tenafly, NJ (US); Luba Chigirinskaya, Brooklyn, NY (US); Marika Cherfas, Brooklyn, NY (US)

( * ) Notice: Subject to any disclaimer, the term of this patent is extended or adjusted under 35 U.S.C. 154(b) by 0 days.

(21) Appl. No.: 14/987,376

(22) Filed: Jan. 4, 2016

(65) Prior Publication Data

US 2017/0189662 A1    Jul. 6, 2017

(51) Int. Cl.
| | |
|---|---|
| *A61N 1/00* | (2006.01) |
| *A61N 2/00* | (2006.01) |
| *A61N 5/067* | (2006.01) |
| *A61N 7/00* | (2006.01) |
| *A61M 37/00* | (2006.01) |
| *A61K 39/395* | (2006.01) |
| *A61N 5/06* | (2006.01) |

(52) U.S. Cl.
CPC ... *A61M 37/0092* (2013.01); *A61K 39/39516* (2013.01); *A61N 2/002* (2013.01); *A61N 5/062* (2013.01); *A61M 2037/0007* (2013.01); *A61N 2005/067* (2013.01)

(58) Field of Classification Search
CPC ............ A61N 1/205; A61N 2007/0021; A61N 2007/0039; A61N 2005/067; A61N 1/3606; A61N 2/00; A61N 2/004; A61N 5/00; A61N 5/10; A61N 5/06

See application file for complete search history.

(56) References Cited

U.S. PATENT DOCUMENTS

| | | | | |
|---|---|---|---|---|
| 5,470,846 | A * | 11/1995 | Sandyk | A61K 31/122 514/159 |
| 2002/0098153 | A1 * | 7/2002 | Allen | A61K 49/085 424/9.364 |
| 2005/0020945 | A1 * | 1/2005 | Tosaya | A61H 23/0236 601/2 |
| 2008/0125836 | A1 * | 5/2008 | Streeter | A61N 5/0618 607/89 |
| 2009/0156884 | A1 * | 6/2009 | Schneider | A61N 2/02 600/14 |
| 2014/0193440 | A1 * | 7/2014 | Clerici | C12Q 1/6883 424/184.1 |
| 2016/0008628 | A1 * | 1/2016 | Morries | A61N 5/0622 607/89 |

* cited by examiner

*Primary Examiner* — Christine H Matthews
*Assistant Examiner* — Joshua D Lannu
(74) *Attorney, Agent, or Firm* — Henry M. Feiereisen LLC.

(57) ABSTRACT

A method and system for treating patients with Alzheimer disease includes steps and equipment operative for subjecting a patient suffering from Alzheimer disease to a non-invasive action directed toward a patient's brain and causing a cavitation process in the patient's brain liquid in the vicinity of lesions and thereby destroying the latter.

2 Claims, No Drawings

METHOD AND SYSTEM FOR TREATING PATIENTS WITH ALZHEIMER DISEASE

BACKGROUND OF THE INVENTION

The present invention relates to methods and systems for treatment of Alzheimer disease.

Alzheimer disease affects millions of people worldwide. It affects brain functions of people suffering from the disease, which results in loss of memory, inability of functioning in everyday life, inferior interaction with other people and environment, and other highly negative effects. It is believed that the disease causes disruption of cell-to-cell communication and also transportation of essential materials such as nutrients and organelles in the brain of a person suffering from the disease.

The reason for this disruption is a formation in the brain of structures or lesions which are on the way of the above specified communication and transportation, such as amyloid plaques, neurofibrillary tangles etc. While amyloid plaques are located between the neurons and form clusters of beta-amyloid molecules, neurofibrillary tangles are found inside the neurons of the brain and form a thick insoluble mass of defective tau proteins which twists filaments or microtubules responsible for the transportation process.

Some medications and treatment methods have been tested, however it is believed that the treatment methods can be improved to more efficiently treat Alzheimer disease.

SUMMARY OF THE INVENTION

Accordingly, it is an object of the present invention to provide a method and a system for treating patients with. Alzheimer disease, which are further improvements of the existing methods and systems.

In keeping with these objects and with others which will become apparent hereinafter, one feature of the present invention resides, briefly stated, in a method of treating patients with Alzheimer disease, which include subjecting a patient suffering from Alzheimer disease to a non-invasive action directed toward a patient's brain and cause a cavitation process in the patient's brain.

Another feature of the present invention resides in that a build-up of lesions is first located in the patient's brain, and the non-invasive action is directed to act on the thusly determined amyloid spot and a brain liquid in their vicinity.

A further feature of the present invention resides in that the build-up of lesions including amyloid plaques and neurofibrillary tangles are located, and non-invasive action is directed to act of the thusly determined amyloid plaques and neurofibrillary tangles and the brain liquid in their vicinity.

A further feature of the present invention resides in that simultaneously with subjecting the patient's brain to the non-invasive action causing the cavitation process, the patient is given gamma-globulin for preventing any side effects which might be causes by the cavitation and for increasing a response of immune system.

A further feature of the present invention resides in that the non-invasive action directed towards the patient's brain and causing the cavitation process can include directing towards the patient's brain electric current pulses with parameters which cause the cavitation process in the patient's brain.

A further feature of the present invention resides in that the non-invasive action directed towards the patient's brain and causing the cavitation process can include directing towards the patient's brain laser pulses with parameters which cause the cavitation process in the patient's brain.

Still a further feature of the present invention resides in that the non-invasive action directed towards the patient's brain and causing the cavitation process can include directing towards the patient's brain acoustic waves with parameters which cause the cavitation process in the patient's brain.

Another feature of the present invention resides, briefly stated, in a system for treating patients with Alzheimer disease, which include means for subjecting a patient suffering from Alzheimer disease to a non-invasive action directed toward a patient's brain and causing a cavitation process in the patient's brain.

Another feature of the present invention resides in that a build-up of lesions are first located in the patient's brain by the system, and the system directs non-invasive action to act on the thusly determined lesions and on a brain liquid in their vicinity.

A further feature of the present invention resides in that means is provided for locating the build-up of lesions including amyloid plaques and neurofibrillary tangles, and means is provided for non-invasive action directed to act of the thusly determined amyloid plaques and neurofibrillary tangles and on the brain liquid in their vicinity.

A further feature of the present invention resides in that means is provided for simultaneously with subjecting the patient's brain to the non-invasive action causing the cavitation process, giving the patient gamma-globulin for preventing any side effects which might be causes by the cavitation and increasing an immune system response.

A further feature of the present invention resides in that the means for non-invasive action directed towards the patient's brain and causing the cavitation process can include means directing towards the patient's brain electric current pulses with parameters which cause the cavitation process in the patient's brain.

A further feature of the present invention resides in that means for the non-invasive action directed towards the patient's brain and causing the cavitation process can include means directing towards the patient's brain laser pulses with parameters which cause the cavitation process in the patient's brain.

Still a further feature of the present invention resides in that means for the non-invasive action directed towards the patient's brain and causing the cavitation process can include means directing towards the patient's brain acoustic waves with parameters which cause the cavitation process in the patient's brain.

The novel features of the present invention are set forth in particular in the appended claims.

The invention itself however both as to its subject matter and manner of operation, will be best understood from the description of the preferred embodiments.

DESCRIPTION OF THE PREFERRED EMBODIMENTS

According to the present invention which is set forth in the patent application, a patient which has symptoms of Alzheimer diseases has to be subjected first to examination for diagnostic purposes.

The examination can be conducted in accordance with known procedures and with known means or equipment, and it first includes determination of external factors which are symptomatic of the disease. Once it is determined that the patient's symptoms are indicative of Alzheimer disease, the patient needs to undergo examination of his/her brain, which can include for example X-ray, Magnetic Resonance Imaging, and others. The objective of the tests is to clarify the location of abnormal lesions or structures in the brain.

Once the location of the lesions, which are formed by amyloid plaques and neurofibrillary tangles is clarified, the lesions in the brain of a patient and a brain liquid in the vicinity of them are subjected according to the present invention to a non-invasive action which causes a cavitation in the brain liquid (fluid) near the lesions by corresponding means which cause the cavitation process. The cavitation which is carried out is a non-inertial cavitation and carried out non-invasively, induces in the environment of the brain liquid (fluid) near the lesions nano-cavities or nano-bubbles which cause a mechanical agitation destroying the lesions.

Corresponding means produce actions which propagate through a brain or bran's tissues and interact with a liquid in the brain, and create a cavitation process in it resulting in formation of nano-bubbles. When the nano-bubbles which can oscillate meet on their way a dense material of the lesions, they collapse and destroy them. As a result, transportation of essential materials and transmission of information in the brain can be restored.

In addition, the cavitation enhances circulation processes in lymphatic vessels in the brain and therefore enhances transportation of the products of destruction of the lesions which are responsible for Alzheimer disease. The enhanced circulation processes in the brain liquid also prevent formation of new lesions.

Various processes and means or equipment which generate cavitation can be utilized according to the present invention.

The non-invasive action which generates cavitation processes in the brain liquid near the lesions in the patient's brain can be executed, for example, by using electric current pulses, in particular remotely applied induction current pulses, directed to the brain and thus to the lesions and the brain fluid around them by means or an apparatus generating and directing such current pulses. In particular electric current can be simulated by electromagnetic induction. A magnetic field generator or coil can be placed near the head of a patient and produce electric current in the region of the brain just under the coil. The magnetic field pulses of about 10-20 Hz reach into the brain for 1-5 cm and can induce electric current of 0.1-10 mA causing cavitation. The treatment can continue for several minutes.

The non-invasive action which generates cavitation processes in a brain liquid near the lesions in the patient's brain can be executed, for example, by using laser pulses directed to the brain and thus to the lesions and the brain liquid around them, with the use of such means as a corresponding laser generator. A laser beam generator can generate infrared radiation with a wave length 5-10 mcm of 1-10 Wt and pulses f 60-150 ns. Its power is enough to penetrate 6-7 cm, following by low energy supply of 10-100 Wt to induce cavitation.

The non-invasive action which generates cavitation processes in the lesions in the patient's brain can be executed, for example, by using acoustic pulses directed to the brain and thus to the lesions and the brain liquid around them. An electronic sonic generator with a driver, an amplifier and a transducer can generate a sine, pulse or square waves within a range of 20-200 Hz and SPL of 130 DB. Acoustic vibrations aimed at the brain can start with lower frequencies of shorter length of 10 msec and increase to 2 sec.

The sessions can be repeated 2-3 times a day. The cavitation process in brain liquid (fluid) caused in the lesions loosens the amyloid plaques and neurofibrillary tangles, etc. and eventually they disappear. Periodical examinations of the brain should be then conducted to follow the progress of the cavitation-induced loosening of the lesions until they are completely cleared.

It is further possible to cause cavitation processes for the treatment by steps and means providing various combinations of the electric current pulses, laser pulses, and acoustic pulses, in accordance with the present invention According to the present invention, it is also suggested that a patient which is subjected to the above described non-invasive cavitation-causing treatment, is given by corresponding means gamma-globulin, preliminarily to the cavitation-causing actions and also between the treatment sessions. Gamma-globulin intake stimulates immune system and also protects healthy matter of the brain from a damage. On the other hand, the cavitation process can eliminate possible infections which can be accidentally present in the gamma-globulin It should be mentioned that the present invention is not limited to the details shown since various modifications and changes are possible without departing from the spirit of the invention.

What is desired to be protected by Letters Patent based on this patent application describing the above-specified invention is set forth in particular in the appended claims.

We claim:

1. A method of treating patients with Alzheimer disease, comprising the steps of:
   subjecting a patient suffering from Alzheimer disease to a non-invasive action selected from the group consisting of electric current pulses, laser pulses, acoustic pulses, and combinations thereof;
   directing the non-invasive action toward a build-up of lesions in a brain of the patient, wherein said lesions include amyloid plaques and neurofibrillary tangles;
   generating by the non-invasive action in a brain liquid of the patient a cavitation process;
   inducing nano-bubbles in the brain liquid of the patient using the cavitation process; and
   destroying the lesions by loosening the amyloid plaques and neurofibrillary tangles using a mechanical agitation caused by the nano-bubbles induced in the patient's brain liquid by the cavitation process.

2. The method of claim 1, further comprising simultaneously with subjecting the patient to the non-invasive action, giving the patient gamma-globulin for preventing any side effects which might be caused by the cavitation process.

* * * * *